(12) United States Patent
Zimmon

(10) Patent No.: US 6,322,522 B1
(45) Date of Patent: Nov. 27, 2001

(54) APPARATUS FOR SEPARABLE EXTERNAL SERIAL COLLECTION, STORAGE AND PROCESSING OF BIOPSY SPECIMENS

(75) Inventor: David S. Zimmon, Port Washington, NY (US)

(73) Assignee: Zimmon Science Corp., Port Washington, NY (US)

( * ) Notice: Subject to any disclaimer, the term of this patent is extended or adjusted under 35 U.S.C. 154(b) by 0 days.

(21) Appl. No.: 09/425,692

(22) Filed: Oct. 22, 1999

Related U.S. Application Data

(63) Continuation-in-part of application No. 09/197,373, filed on Nov. 20, 1998, now Pat. No. 6,071,248, and a continuation-in-part of application No. 08/936,145, filed on Sep. 22, 1997, now Pat. No. 5,980,468, said application No. 09/197,373, is a continuation-in-part of application No.08/936,145.

(51) Int. Cl.[7] .................................................... A61B 5/00

(52) U.S. Cl. ............................................................. 600/565

(58) Field of Search .................................. 600/564–567; 606/167, 170

(56) References Cited

U.S. PATENT DOCUMENTS

| | | | |
|---|---|---|---|
| 5,409,013 | * | 4/1995 | Clement ................................. 600/566 |
| 5,685,320 | | 11/1997 | Zimmon et al. ...................... 128/754 |
| 5,775,333 | * | 7/1998 | Burbank et al. ..................... 600/566 |
| 5,782,747 | | 7/1998 | Zimmon ............................... 600/104 |

FOREIGN PATENT DOCUMENTS

94/24941 * 11/1994 (WO) .

* cited by examiner

*Primary Examiner*—Max Hindenburg
(74) *Attorney, Agent, or Firm*—Collard & Roe, P.C.

(57) ABSTRACT

An apparatus for performing a medical procedure, comprising an elongated flexible member having an aperture extending longitudinally therethrough and an actuator positioned within the aperture. There is a biopsy means connected to the distal end of the actuator for cutting and collecting biopsy specimens and a storage and collection chamber connected to the elongated flexible member for receiving biopsy specimens cut and collected by the biopsy means. The storage and collection chamber is separable from the flexible member and can be sealed by a cap positionable over the storage and collection cassette for storage, processing and in situ or later analysis of biopsy specimens collected by the biopsy means in the order of collection.

9 Claims, 3 Drawing Sheets

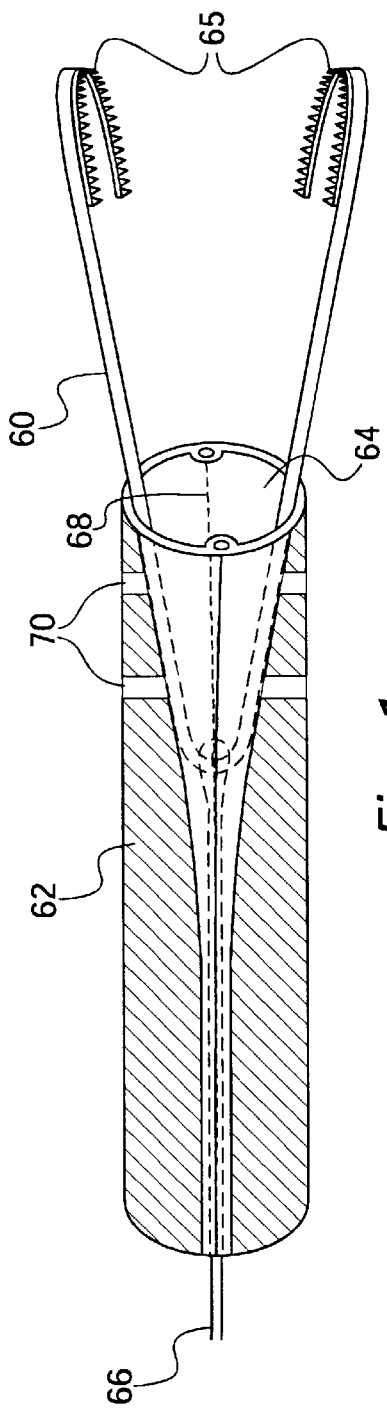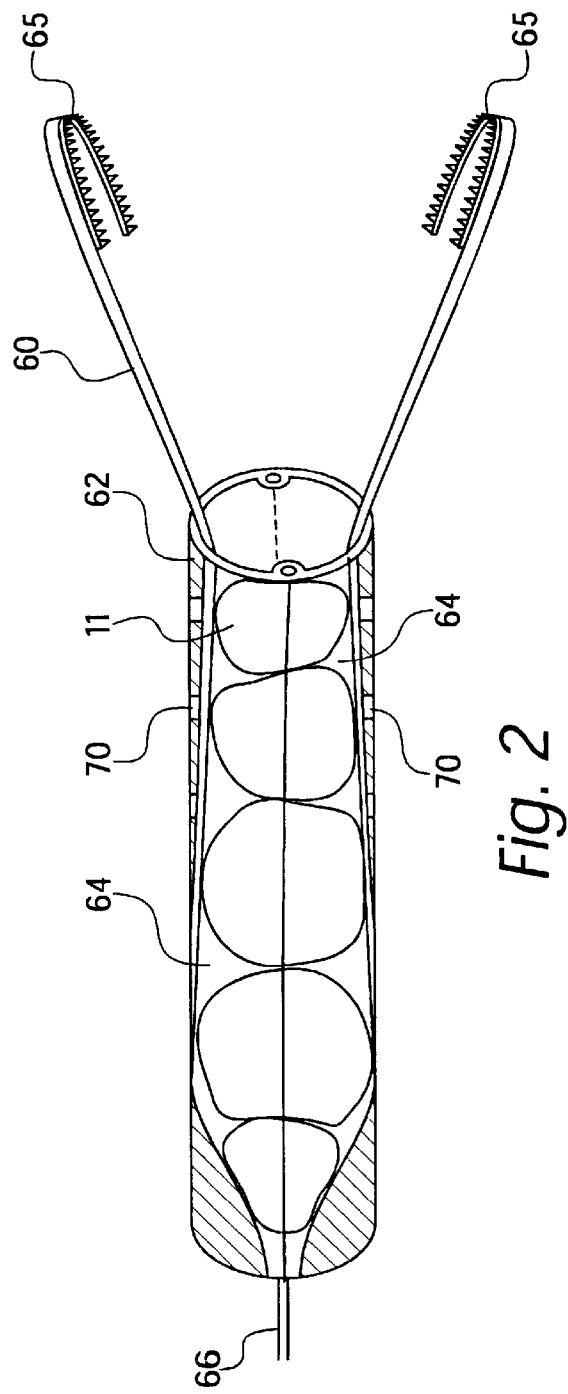

APPARATUS FOR SEPARABLE EXTERNAL SERIAL COLLECTION, STORAGE AND PROCESSING OF BIOPSY SPECIMENS

This application is a continuation-in-part of U.S. patent application Ser. No. 08/936,145, filed on Sep. 22, 1997 now U.S. Pat. No. 5,980,468 and U.S. patent application Ser. No. 09/197,373, filed on Nov. 20, 1998 now U.S. Pat. No. 6,071,248 which is a continuation-in-part of U.S. patent application Ser. No. 08/936,145, now U.S. Pat. No. 5,980,468.

BACKGROUND OF THE INVENTION

1. Field of the Invention

The present invention relates to an apparatus for collection, storage and processing of biopsy specimens. The device cuts and captures a biopsy specimen with a closely defined size to permit entry into a storage cassette for subsequent processing.

2. The Prior Art

It is often necessary to obtain tissue samples for examination from deep within structures. These samples can only be retrieved by catheterization methods using endoscopic or fluoroscopic control, or by blind palpation. The biopsy devices used for these techniques remove 1 to 4 specimens that are retrieved by removing the biopsy instrument from the patient, and placing the specimen in a container of fixative solution labeled with the biopsy site and patient identification. The biopsies obtained in each pass are processed in a batch, since the minute pieces cannot be easily separated. Consequently, biopsies from different sites must be handled separately, thus requiring considerable effort and expense. Multiple biopsy passes are required because of the limited storage capacity of the biopsy instruments and the need to identify the sites of biopsy origin. This prolongs the procedure and may even cause it to fail, if the position of the biopsy instrument cannot be reacquired.

The batch of containers for each patient is then transported to the laboratory where the containers are serially opened and the specimens transferred to numbered cassettes that are recorded for later identification. The cassettes are then processed for examination. The processed specimens are then sliced, stained and mounted on labeled slides for microscopic examination. The specimens in each container must be processed separately to maintain identification. This is particularly important when the distribution and extent of a cancer is being mapped to determine the possibility of surgical removal and to prevent errors in reporting.

During this complex handling process, small specimens may be lost or damaged. At each stage of handling, the staff is exposed to possible infection from the biopsies, which is particularly true when the unfixed specimen is removed from the sharp biopsy instrument before it is fixed. The staff is also exposed to solvent vapor from the fixative at each transfer step of processing. The solvents may be allergenic or carcinogenic. This tedious, labor intensive process is also expensive both in terms of time and laboratory space.

Although the prior art has made biopsy deep within the patient possible, the need for additional improvements remains.

The storage and processing of multiple specimens within a biopsy instrument yields a great savings of time and effort in processing the biopsies, as well as preventing specimen loss or damage during handling. This goal is facilitated by applying redundant methods for forcing the minute biopsy specimens into a storage cassette of the biopsy instrument and by minimizing the operating parts of the biopsy instrument to maximize the storage volume.

The prior art described in the spring based multipurpose medical instrument in U.S. Pat. No. 5,782,747 to Zimmon, the disclosure of which is herein incorporated by reference, obviates the use of cumbersome metal shafts and coverings that occupy the space needed for specimen storage. Standard jaw fulcrum biopsy devices require a stiff shaft to prevent kinking and binding within the endoscope when the actuator cable(s) is pulled to close the biopsy jaws and then held to maintain jaw closure when removing the device and biopsy from the endoscope or access passage. The combined stiffness of the shaft and pull on the actuator cable(s) straightens the biopsy device and endoscope. This action moves the endoscope and biopsy device away from the biopsy site and limits maneuverability. This stiffness and uncontrolled motion also risks trauma to the biopsy site and limits access in curved lumens. A further limitation of stiff shafts is that they reduce the options for carrier instrument flexibility and maneuverability.

The closing force of a traditional forceps biopsy instrument is limited by a shaft length ranging from 100 cm to 220 cm and the multiple curves traversed within the endoscope that must conform to a lumen. Because of these disabilities, endoscopic biopsy forceps that are 5 to 9 French in diameter rip the mucosal biopsy from the muscularis mucosa. This gives a biopsy that is larger than the forceps cup and varies in size. Furthermore, tissue distortion from biopsy trauma may make histopathologic interpretation difficult.

U.S. Pat. Nos. 5,685,320 and 5,782,747, both to Zimmon, both of which are herein incorporated by reference, solve this problem by sharply cutting a biopsy of defined size that is suitable for passage through the tube shaft to an external receptacle. In U.S. Pat. No. 5,782,747, the distance between the central actuator wire and the cutting blade controls biopsy depth. Consequently, biopsy depth is less than one half of the shaft diameter. Actuator wire movement that limits the length of the cutting notch controls biopsy length. Width of the tangential biopsy is less than one half the tube shaft circumference. The cut biopsy is then captured within the tube shaft at the time of biopsy and therefore available to move into the external collection cassette.

In U.S. Pat. No. 5,685,320, the spring based multipurpose medical instrument compresses folded spring sharp biopsy cups by sliding the tube shaft over a folded spring. The actuator wire only serves to hold the folded spring blade in biopsy position during biopsy cutting. The closed biopsy cups both cut and capture a biopsy of controlled size that is matched to the tube shaft and therefore available to move into the storage cassette.

The motive force of suction or fluid pressure propels the precisely cut biopsy from either device into the distal collection cassette as described in U.S. patent application Ser. Nos. 08/936,145, and 08/197,373 the disclosures of which are also herein incorporated by reference.

SUMMARY OF THE INVENTION

It is therefore an object of the present invention to provide an external biopsy collection, storage and processing cassette that is simple to use and provides a convenient external storage cassette for processing of the collected biopsy specimens.

The device according to the invention comprises a flexible plastic shaft with one or two side lumens and a relatively large central lumen. In the spring based instrument, the distal end contains a remotely controllable folded spring jaw biopsy device of the type described above within the central lumen, that is stabilized by metal or plastic guides. Plastic or metal guides are preferably inserted into the central lumen of the catheter to support and prevent twisting of the folded spring and to create a chamber for the storage of biopsies. The guides enlarge the lumen and ensure that there is sufficient room to store the collected biopsy specimens as compared to a solid plastic extrusion with only a slot as a guide. It also enables the use of a simple extruded catheter for the device. The folded spring jaw is extended proximally to form a chamber within the shaft to receive the specimens.

The junction of the chamber and the spring jaw is angulated to increase the distance between the jaws when they are extended and also to form a constriction at the distal most end of the chamber. The constriction and holding chamber remain within the shaft and prevent loss of the stored biopsies. As the spring jaws are drawn into the shaft with each new biopsy, the constriction is reduced, allowing the latest specimen to be aspirated into the holding chamber. There are side lumens(s) having open slits in the shaft to carry suction from the proximal end of the catheter to draw the specimens into the chamber after each biopsy.

Since the tube shaft or catheter is passed to the biopsy site within a loosely fitting endoscope instrument channel, it is constrained by the endoscope channel. Only the few centimeters of the biopsy device outside the distal end of the endoscope are unsupported.

Advancing the tube shaft within the constraining endoscope channel closes the jaws with little tendency to kink the tube shaft. The action of the tube shaft in moving forward to close the jaws, while the flexible actuator cable is held in place, ensures that the closed spring jaw remains at the desired biopsy site. This movement control facilitates multiple target biopsies with minimum repositioning the endoscope or biopsy instrument. The capture of the biopsy jaws by the tube shaft at each biopsy moves the biopsy toward the shaft and facilitates transfer of each specimen to the tube shaft storage cassette.

After the specimens have been collected, the spring jaws are removed and the distal end of the shaft is capped. The shaft is cut at a marked site proximal to the specimen holding chamber and capped with a second cap. Perforated caps allow fixation and processing of the specimens within the chamber. The shaft has thus become a processing cassette with the serial specimens enclosed in order of acquisition and ready for fixation and processing without further handling.

After processing to wax, the closed shaft is cut open and the biopsies are ready for slicing, still remaining in order of acquisition. Thus, a single log prepared at the time of biopsy serves to identify each specimen to the submitter and laboratory, and for reporting without handling, risk of biopsy loss or documentation error.

This invention has the option for use without an endoscope through a second external bendable tube shaft. The external tube shaft may be plastic, metal or any bendable material. The operator forms and inserts the tube shaft into the biopsy site. A spring based biopsy instrument of chosen diameter and flexibility is passed through the outer shaft to perform a biopsy or other operation. Operation of this invention may be monitored radiologically, visually, by palpation or any alternative.

One embodiment of the improved design for the cutting biopsy jaws is to provide multiple perforations in the spring metal jaw. The perforations allow air or fluid injected through the endoscope to entrain the biopsy toward the proximal suction slits in the storage chamber. This entrainment adds to the suction force in propelling the biopsy proximally.

A second embodiment for moving the biopsy proximally from the jaws into the storage chamber is to forcibly inject fluid from the proximal end of the tube shaft distally into the closed jaws containing the captured biopsy. The fluid is injected through channels molded into the tube shaft. In this embodiment, there are perforations in the storage chamber that facilitate movement of the injected fluid stream back to storage chamber to entrain the biopsy proximally as the injectate exits the storage chamber through the perforations. Each successive biopsy capture and injection compresses the biopsies proximally to maximize the number of biopsies stored and to prevent mixing.

These operations are facilitated by the capture of the biopsy jaws by the shaft with each closure. Perforations in the storage chamber also accelerate the access of fixative and processing fluid when the storage cassette is cut from the shaft for fixation and prepared for analysis. Similarly, the lateral biopsy instrument captures each biopsy as it is cut. Thus biopsies can be forced proximally through the entire tube shaft to exit at a side port and return to the operator for immediate inspection and analysis, instead of forming the cassette by cutting the tube shaft and using the caps previously described.

In a preferred embodiment of the present invention, the serial collection, storage and processing cassette is positioned outside an endoscope attached to a side arm of the biopsy instrument. Selection of a defined reproducible biopsy size to traverse the biopsy mechanism and into the tube shaft to enter a distal storage cassette makes it feasible to force the biopsy through the entire tube shaft to an external side outlet and then into an external cassette. The related objects and advantages of the present invention will be apparent from the following description.

BRIEF DESCRIPTION OF DRAWINGS

In the drawings, wherein similar reference numerals denote similar elements:

FIG. 1 shows a side cross-sectional view of a device according to the invention;

FIG. 2 shows a side cross-sectional view of the device according to FIG. 1 with the jaws extended;

DESCRIPTION OF PREFERRED EMBODIMENTS

Figure 3:
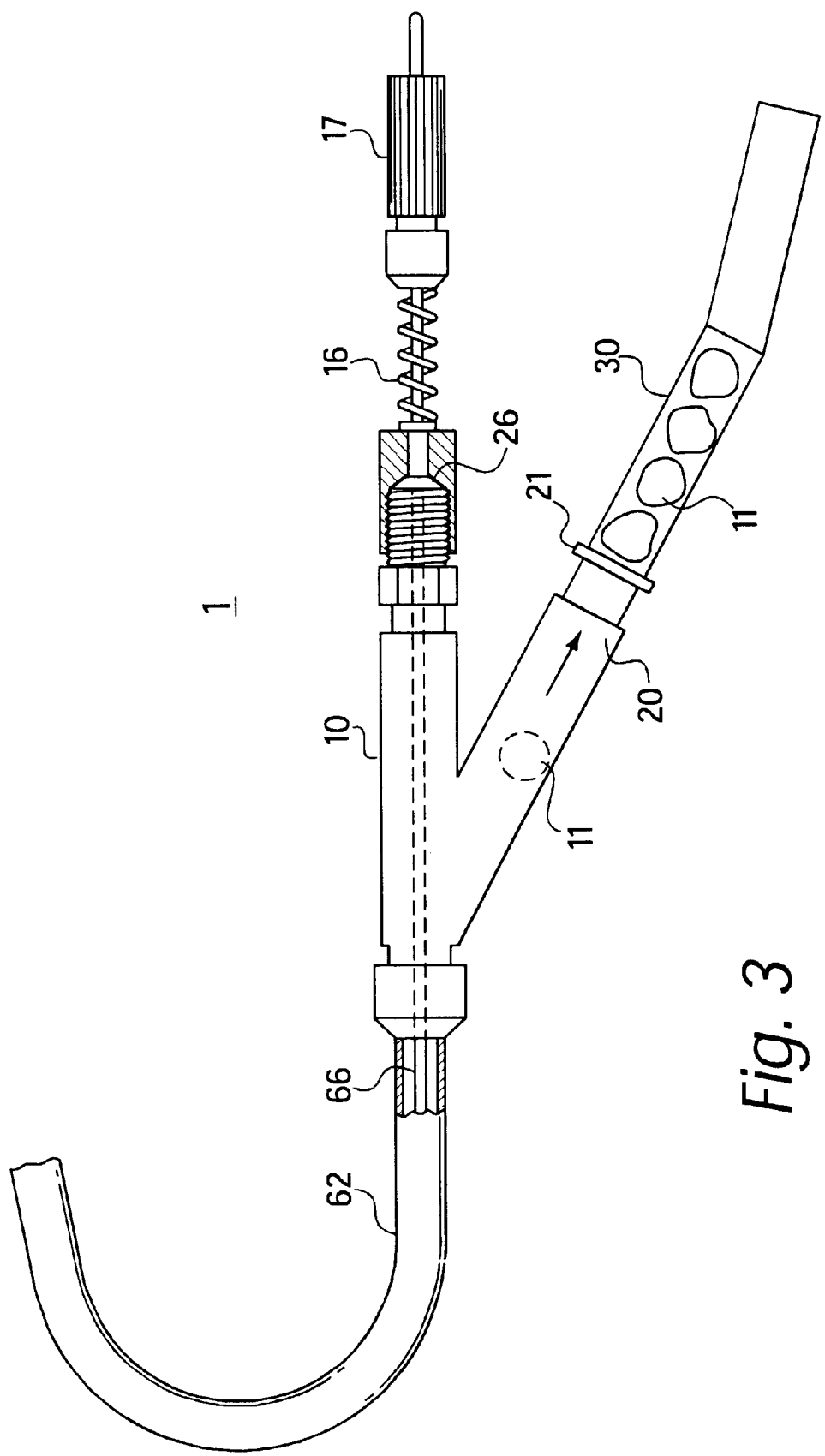
FIG. 3 shows an alternative embodiment of the invention having an external cassette containing four biopsies removably attached to the sidearm of the device.

For purposes of promoting and understanding the principles of the invention reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIGS. 1 and 2 show the device according to the invention, which retrieves specimens 11 through a spring-based biopsy cutting tool 60. Cutting tool 60 is arranged inside a catheter 62, which has two small side lumens 63 and a large central lumen 64. Central lumen 64 has a plurality of jaw guides 70 which act as a specimen holding chamber, as shown in FIG. 2. Jaw guides 70 could be made of any suitable material such as metal or plastic. Cutting tool 60 has two spring-based jaws equipped with two open-faced cutting blades 65 on each jaw of cutting tool 60.

Cutting tool 60 is deployed to cut and retrieve biopsy specimens, and to bring the specimens inside catheter 62 for storage. The movement of tool 60 is controlled by actuator wire 66, which, when pulled, causes the tool 60 to retract and blades 65 to come together to cut specimen 11. Further pulling on wire 66 causes tool 60 to retract inside lumen 64 and pull specimen 11 inside as well. Alternatively, the tube shaft is advanced over the spring jaws while holding the actuator wire in place forcing the jaws closed to cut the biopsy. After specimen 11 is deposited inside lumen 64, tool 60 can then be deployed to cut and retrieve additional specimens.

Side lumens 63 are connected to lumen 64 through a plurality of slits 68. Suction can be applied to side lumens 63 at the proximal end of catheter 62, which is then carried into central lumen 64 through slits 68 to draw specimens 11 into central lumen 64 after each biopsy.

Figure 4:
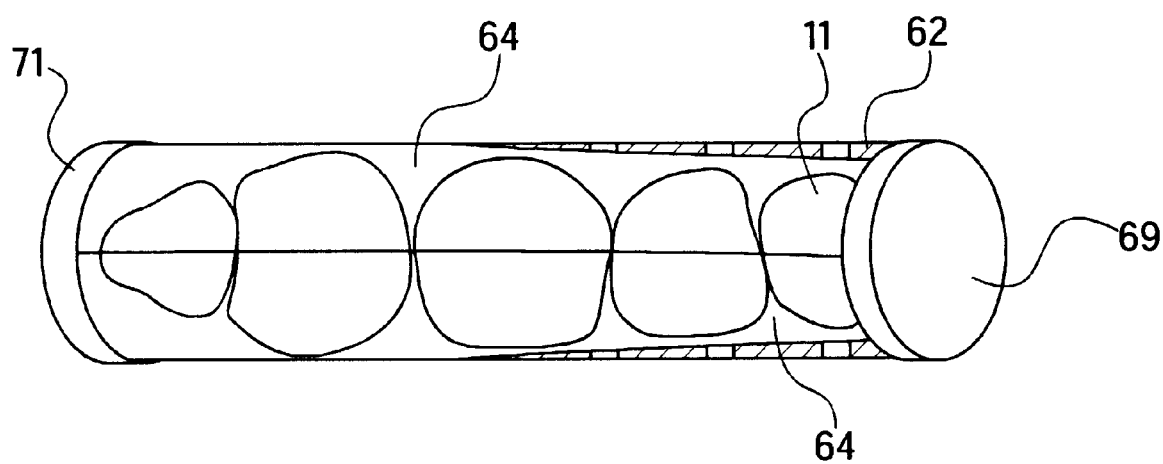
FIG. 4 shows an external cassette separated from the device according to the invention.

When the desired number of specimens 11 have been collected, tool 60 is removed from catheter 62 and the distal end is capped with a perforated cap 69, as shown in FIG. 4. Perforated cap 69 allows for addition of fixative to the specimens during storage in lumen 64. Catheter 62 is then cut at a specified site at its proximal end and capped with a cap 71, thus creating a processing cassette whereby the specimens can be processed in order of acquisition without the preparation of additional logs or excessive handling of specimens 11.

In a preferred embodiment, which is shown in FIG. 3, the serial collection, storage and processing cassette 30 is positioned outside the biopsy instrument shaft 10. The biopsy is collected in the manner shown in FIGS. 1 and 2, using jaws 65 or with the lateral biopsy device shown in U.S. Pat. No. 5,685,320, and then transferred through catheter 62, through instrument shaft 10, and down side arm 11 into cassette 30. Cassette 30 can be easily removed from mounting plate 21, and capped in the same manner as shown in FIG. 4. Additional cassettes 30 can then be mounted to mounting plate 21 for the capture of additional biopsies 11. This obviates the need to sacrifice the biopsy instrument when forming the processing cassette.

To collect each biopsy 11, handle 17 is pushed against spring 16 on the instrument 1, which causes jaws 65 to deploy and collect the biopsy. Thereafter, handle 17 is retracted, pulling actuator wire 66, causing jaws 65 to retract back into catheter 64 with biopsy 11, as described above. Alternatively the tube shaft is advanced to close and capture the spring jaw within the shaft. Suction exerted by suction control 26 then forces biopsy 11 to travel into cassette 30.

The biopsy instrument 1 with external cassette 30 can be washed, disinfected and reused. Consequently a more expensive reusable design may replace a disposable instrument yet the advantages of serial collection, storage and processing retained.

A further advantage is immediately available multiple cassettes 30 for segregation of biopsies for multiple and immediate analysis without removing the biopsy instrument from the endoscope during a procedure. Thus separate biopsies can be obtained in individual cassettes for chemical, biological, genetic, frozen section or fixed pathologic analysis. This is advantageous since each type of analysis requires different handling.

Further, an external cassette 30 can be modified in size and shape that otherwise would be incompatible with the limitations of a biopsy instrument tube shaft that must conform to the long narrow endoscope instrument channel. The cassette is closed by capping (shown in FIG. 4), clipping, crushing or heat sealing (not shown). The captured specimens 11 then can be inspected for adequacy by using an optically transparent cassette material, fixed, refrigerated, frozen or transported for analysis. The procedure can continue and additional biopsies can be acquired with the biopsy instrument in place.

In contrast to the present invention, most current biopsy instruments must be removed from the endoscope to retrieve the specimen and begin processing after each or at most a few biopsies are taken. This action is often accompanied by endoscope movement the may require repositioning of the endoscope or even loss of position rendering additional biopsies impossible. These delays prolong the procedure and period of anesthesia. The risk of the procedure complications and cost is thereby increased.

A storage cassette external to the endoscope permits use of a storage cassette of a size, shape and character that could not be accommodated by the narrow endoscope instrument channel and biopsy instrument tube shaft. A variety of cassettes and cassette functions can then be provided. Tissue analysis can be performed on biopsies within the cassette and the results are immediately available to the operator. Thus complex analysis such as endoscopic laser reflectance spectroscopy followed by biopsy would be replaced by biopsy with external reflectance spectroscopy of the biopsies within the cassette. The complex expensive laser endoscope would be replaced by external spectroscopy and the biopsies immediately available for other chemical, biological, enzymatic, histopathologic and other types of analysis. Within the cassette, in vivo tissue staining with methylene blue, Lugols iodine, indigo carmine or other stains would obviate the need to spray dyes onto the mucosal surface.

The commonly used dip stick chemical or biological assays can easily be incorporated into a visible external cassette for immediate detection of tissue abnormalities such as infection, dysplasia or frank neoplasia. For example, diagnosis of gastrointestinal mucosal infection with H. pylori currently requires that a biopsy be obtained and either submitted to microscopic examination after fixation and staining, requiring days, or be incubated with chemicals to demonstrate the presence of the enzyme urease by conversion of urea to ammonia. This analysis system can easily be incorporated into an external cassette that yields an immediate result. If positive, the diagnosis is established and no additional biopsies are needed. If negative, additional biopsies would be obtained and tested to confirm. The biopsies could then be submitted to microscopic examination for confirmation by pathologic analysis. This yields an important saving in procedure time with the patient under anesthesia, limits handling of potentially infectious tissue by staff, and delay in diagnosis and reduces cost.

The pathology laboratory has difficulty in orienting free floating minute biopsy specimens for wax embedding, sectioning and microscopic study. Considerable time and effort are spent in biopsy orientation. A poorly oriented biopsy may obscure or yield a false diagnosis. A false negative diagnosis may force another procedure. A false positive diagnosis may precipitate unnecessary treatment. The pathologist may equivocate when interpreting a biopsy because of these well known problems.

The external storage cassette 30 solves these problems by orienting the biopsy within the cassette. An external cassette lumen 1.5 deep by 3.5 mm wide conforms to the biopsy size of 1 mm deep, 3 mm long and 2 mm wide, so the biopsy will be forcibly oriented in the cassette. Alternatively, a larger cassette allowing free movement of the biopsy and provided with an adherent surface such as fibrin or albumin would cause adhesion of the cut, sticky non-mucosal surface to orient the biopsies flat on the adherent surface with the non-adherent mucosal side up. Numerous sulfated substance known to adhere to the mucosal surface such as carageenan, sulfated amylopectin and sulfated sucarafate could serve as the adherent surface for the mucosal side of the biopsy.

What is claimed is:

1. An apparatus for performing a medical procedure, comprising:

an elongated flexible member having an aperture extending longitudinally therethrough, said member having a proximal and an opposite distal end;

an actuator positioned within the aperture, said actuator having a proximal end and an opposite distal end;

biopsy means connected to the distal end of the actuator for cutting and collecting biopsy specimens of controlled size;

a storage and collection cassette removably connected to said elongated flexible member by a side arm for receiving biopsy specimens cut and collected by the biopsy means, wherein the storage cassette has an internal adhesive surface to adhere a cut or mucosal biopsy surface and thereby orient collected biopsy specimens in the storage chamber;

means for moving the biopsy from the biopsy means to the side arm and then into the cassette; and means for sealing the storage cassette when said storage cassette has been separated from the flexible member for storage and processing of biopsy specimens collected by the biopsy means in the order of collection.

2. The apparatus of claim 1, wherein storage cassette incorporates a means for chemical, biological or genetic analysis.

3. The apparatus of claim 1, wherein the storage cassette incorporates tissue fixative or stain.

4. The apparatus of claim 1, wherein the storage cassette is translucent for visual inspection or spectrometry.

5. The apparatus of claim 1, wherein the biopsy means comprises a spring jaw having a cutting tool, said spring jaw being remotely deployable from said flexible member, and an internal jaw guide in the distal end of said member, said jaw guide controlling the precise movement of said jaw and defining a cavity within said member for receiving a substantial portion of said jaw to provide a defined biopsy size.

6. The apparatus of claim 1, wherein the sealing means is a cap positionable over said storage cassette when said cassette is separated from the flexible member.

7. The apparatus of claim 6, wherein the cap is perforated.

8. The apparatus according to claim 1, wherein the storage cassette is removably connected to the flexible member, and wherein additional storage cassettes are positioned on the flexible shaft when said storage cassette is filled with biopsies and removed.

9. The apparatus according to claim 1, further comprising means for applying suction to the flexible member to force collected biopsy specimens from the flexible member into the storage cassette.

\* \* \* \* \*